United States Patent [19]

Shiga

[11] 4,334,545
[45] Jun. 15, 1982

[54] BIOFEEDBACK SYSTEM

[75] Inventor: Kazumasa Shiga, Kawasaki, Japan

[73] Assignee: Matsushita Electric Industrial Company, Limited, Osaka, Japan

[21] Appl. No.: 97,985

[22] Filed: Nov. 28, 1979

[30] Foreign Application Priority Data

Nov. 28, 1978 [JP] Japan ................. 53-147449

[51] Int. Cl.$^3$ ............................................. A61B 5/04
[52] U.S. Cl. ................................................. 128/732
[58] Field of Search ............................ 128/731-733

[56] References Cited

U.S. PATENT DOCUMENTS

| | | | |
|---|---|---|---|
| 3,032,029 | 5/1962 | Cunningham | 128/732 |
| 3,656,474 | 4/1972 | Gentry et al. | 128/733 X |
| 3,774,593 | 11/1973 | Hakata et al. | 128/733 |
| 3,863,625 | 2/1975 | Viglione et al. | 128/732 |
| 3,924,606 | 12/1975 | Silver et al. | 128/732 |
| 3,942,516 | 3/1976 | Glynn et al. | 128/733 |
| 3,945,374 | 3/1976 | McClure | 128/733 X |
| 3,978,847 | 9/1976 | Fehmi et al. | 128/733 |
| 4,228,807 | 10/1980 | Yagi et al. | 128/732 |

OTHER PUBLICATIONS

Ray, C. D., "Quantitative Techniques in EEG", in *Medical Engineering*, Yrbk. Publ., Chicago, Ill., 1974, pp. 385-386.

*Primary Examiner*—Robert W. Michell
*Assistant Examiner*—Francis J. Jaworski
*Attorney, Agent, or Firm*—Lowe, King, Price & Becker

[57] ABSTRACT

Mental activity of a human subject is indicated with electrodes placed on the head of the subject to respond to brain activity. The electrodes derive a signal including low and high frequency a.c. components respectively having frequency ranges in the same low frequency range as alpha waves derived by the brain and considerably higher than the highest frequency of the alpha waves. The high and low frequency amplitude components are supplied to an indicator arranged so the mental state activity is indicated only in response to the detected high frequency component having an amplitude less than a level indicative of the subject not being in a state of relaxation and the detected low frequency component having an amplitude greater than a first predetermined value and less than a second predetermined value. The low frequency amplitude between the first and second predetermined values is associated with the alpha waves.

22 Claims, 1 Drawing Figure

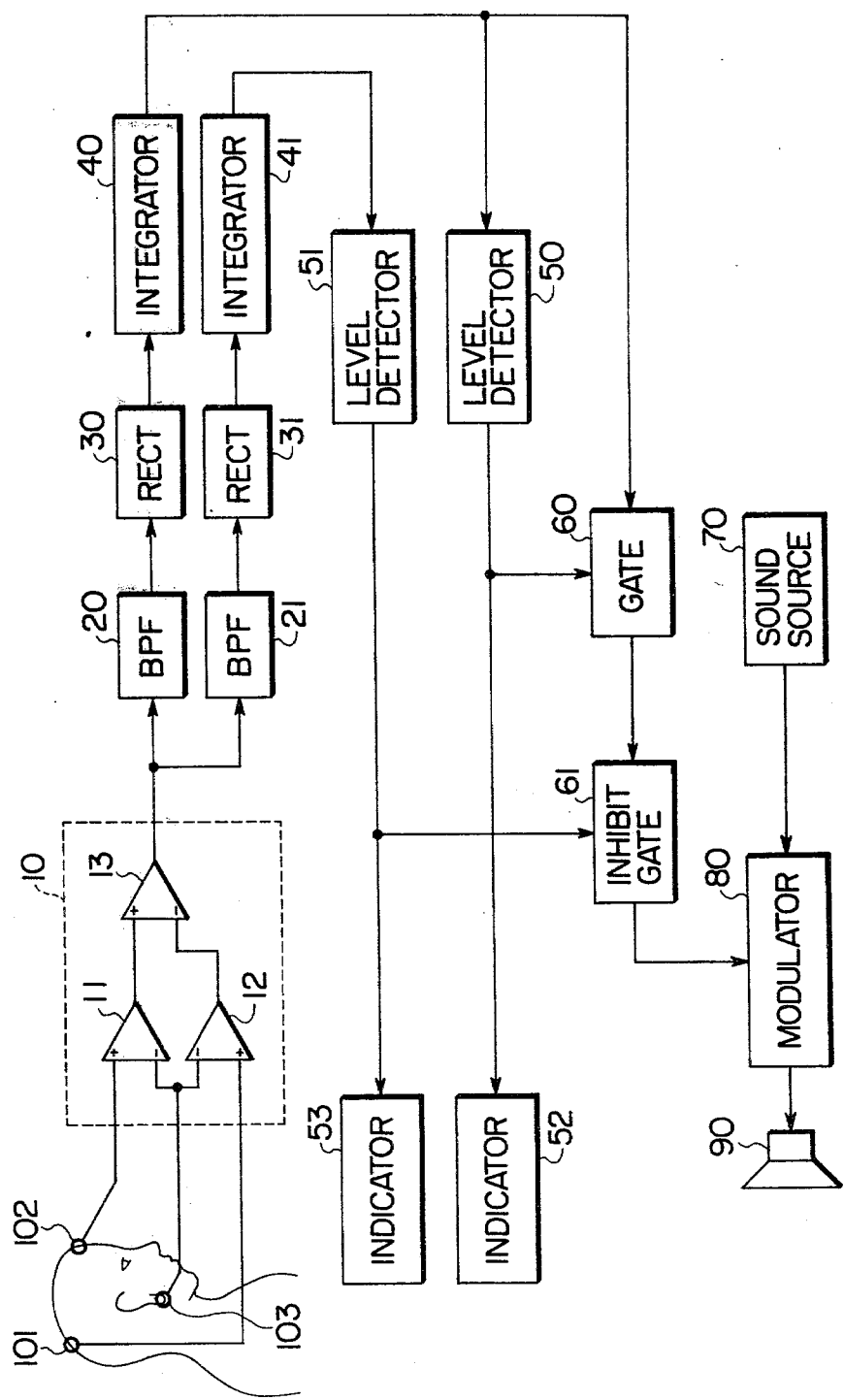

BIOFEEDBACK SYSTEM

BACKGROUND OF THE INVENTION

The present invention relates to a biofeedback system which is used for indicating the state of mental activity of a human subject.

It is well known that human mental activity can be measured in terms of (1) electrical activity of the brain as represented by the brain waves, (2) electrical potential changes measured by electromyographic method, (3) potential changes at the surface of the skin or (4) temperature at the skin surface. It is also known that these physiological phenomena can be used to control the autonomic nerve system of the human subject or used as a means for rehabilitation. More specifically, when a human subject is in a relaxed state of mind, the predominant brain waves are the so-called alpha waves and the muscle potential falls to a low level, while there are increases in the electrical resistance and temperature of the skin. Conversely, when the subject is in a nervous, strained or highly excited state, the beta waves are predominant, the muscle potential becomes high and there are decreases in the electrical resistance as well as temperature of the skin.

Thus, an indication of such physiological signals can serve as a guide to lead the human subject into a relaxed state of mind. This kind of mind control is called "biofeedback" and apparatus used for such purposes is part of a biofeedback system.

However, because the presence of a single physiological signal is not necessarily a true indication of relaxation it is desired that there be as many sources of physiological clues as possible. One approach to this problem seemingly is to combine a plurality of specific measurement devices in a single unit for simultaneous indication of the measured data. This approach however requires the user constantly to scan his eyes over the displayed data. Because of this factor the use of plural measurement devices appears to be unsatisfactory as a guide for mind control purposes.

SUMMARY OF THE INVENTION

A solution to the aforesaid problem is obtained by generating an inhibit signal when a desired state of mind is not yet achieved and nullifying a main physiological signal in response to the inhibit signal even if the main signal gives a strong indication of the presence of a desired state of mind. The main physiological signal may comprise the alpha and/or theta brain wave, and the inhibit signal is derived from another source. In a preferred embodiment, the inhibit signal is derived from a brain wave having a higher frequency than the frequency of the alpha wave when the amplitude of the brain wave is greater than a predetermined value.

BRIEF DESCRIPTION OF THE DRAWINGS

The invention will be further described by way of example with reference to the sole FIGURE which is a schematic illustration of the biofeedback system of the invention.

DETAILED DESCRIPTION

Referring now to the sole FIGURE, active electrodes 101 and 102 are placed on the scalp of a human subject near the sources of electrical activity. Inactive electrode 103 is placed on the earlobe which is relatively distant from the active electrodes. The active electrodes 101 and 102 pick up electrical activity of the brain close to the active electrodes. Electrodes 101 and 102 respond to the brain electrical activity to derive signals that are coupled to the noninverting inputs of operational amplifiers 11 and 12 which form part of a differential amplifier stage 10. The inactive electrode 103 serves as a reference electrode that responds to undesirable electrical noise components to derive a signal which is coupled to the inverting inputs of the operational amplifiers 11, 12. The outputs of the amplifiers 11 and 12 are connected to the noninverting and inverting input terminals of a third operational amplifier 13, respectively, so that the reference signal from the inactive electrode 103 is cancelled in the third amplifier 13. Thereby, the output of the differential amplifier 10 is representative of the difference in amplitude between the signals from the active electrodes 101 and 102. In this way, undesirable noise components which may be introduced into the signals picked up by the active electrodes are reduced to a minimum.

The output signal from the differential amplifier stage 10 is applied to bandpass filters 20 and 21. The bandpass filter 20 has a passband for frequencies from 8 to 14 Hz to detect alpha brain waves. Bandpass filter 21 has a passband for frequencies from about 80 Hz to 1000 Hz to pick up artifact signals contained in the brain waves of higher frequencies which are normally present when the human subject is not in the state of relaxation. The artifact signals are various waves which arise from sources other than the brain.

The signal from the filter 20, which is conveniently called the signal A, is applied to a rectifier 30 to generate unipolar pulses which are applied to an integrator 40. The signal from the filter 21, which is conveniently called the signal B, is applied to a rectifier 31 to generate unipolar pulses as an input to an integrator 41. The time constant value of the integrator 40 is greater than that of the integrator 41; and the typical values of the time constants for integrators 40 and 41 are 1 second and 0.1 seconds, respectively.

The DC signal from the integrator 40 is applied to a level detector 50 which detects the presence of alpha brain waves by comparing the input DC level derived by the integrator with lower and upper voltage levels corresponding respectively to output levels of 10 and 100 microvolts of the active electrodes. When the input DC level falls within this range between the lower and upper voltage levels, the level detector 50 generates a control signal for a gate circuit 60 to enable the output signal from the integrator 40 to pass through gate 60 to an inhibit gate 61.

The DC signal from the integrator 41, on the other hand, is applied to another level detector 51 which generates an inhibit signal signifying the absence of the state of relaxation when the input signal to the detector exceeds a reference level corresponding to the 100-microvolt level of the active electrodes. This inhibit signal is applied to the inhibit gate 61 to prevent the passage of signals from the gate 60 to a modulator 80. This modulator provides amplitude or frequency modulation of a sound program signal, such as musical note, from a sound source 70. The modulated output signal is applied to a loudspeaker 90 which therefore derives an aural signal having a variable intensity or pitch to indicate the presence of brain activity.

During the early stages of an attempt by a human subject attempting to relax the electrical activity of the brain generates relatively high amplitude brain waves of a frequency spectrum which is in the passband of the bandpass filter 21. The resulting outputs of filter 21, rectifier 31 and integrator 41 cause the level detector 51 to produce an inhibit signal so that the audio signal from the source 70 is not modulated, whereby no control signal is applied by gate 61 to modulator 81 and loudspeaker 90 is energized with the unmodulated signal from source 70 to indicate that the subject is not in a relaxed state. When the person enters the state of relaxation alpha brain waves are generated and detected by level detector 50 which enables the gate 60 to pass the signal from the integrator 40 to the inhibit gate 61 and thence to the modulator 80. The sound signal from source 70 is thus amplitude or frequency modulated by the integrated alpha waves derived from detector 50 and the subject is given an indication by the modulated sound from speaker 90 that he is in the relaxed state.

Even if the signal from the integrator 40 has an amplitude falling within the range of detector 50, the state of relaxation may not be reached. In this case the signal from the integrator 41 is of a relatively large amplitude to prevent the inhibit gate 61 from passing to the modulator 80 the signals which have been band-pass filtered and range-detected, but which unreliably indicate relaxation. Thereby a constant tone is derived from speaker 90 to provide an indication that the state of relaxation is not yet reached.

In a preferred embodiment, visual indicators 52 and 53 are connected to the outputs of the level detectors 50 and 51, respectively, to indicate the presence and absence of the signals A and B respectively representing the presence and absence of relaxed state of mind. These visual indications serve to help the human subject to reach the desired state of mind until the audible indication is given by the loudspeaker 90.

The foregoing description is directed only to the preferred embodiment of the invention. Various modifications are apparent to those skilled in the art without departing from the scope of the invention which is only limited by the appended claims. For example, the bandpass filter 20 may have passband frequencies which correspond to the theta brain waves to employ the latter brain waves as a main physiological signal indicating the presence of a relaxed state of mind. Furthermore, the physiological signals may also be obtained from other sources of electrical activities of a human body such as muscle potentials measured by the electromyographic method, skin potentials and temperatures; these signals may also constitute the main physiological signal used to indicate the presence of relaxed state of mind. If muscle potentials, or signal A, are used as a main physiological signal skin potentials are preferred to derive the inhibit signal. If skin potentials were used to derive the main physiological signal, the skin temperature signal is preferred to derive the inhibit signal, and vice versa.

What is claimed is:

1. A biofeedback system comprising, means for sensing electrical activity within a human body to generate a single source signal representing the sensed electrical activity, means for deriving from said source signal a first physiological signal normally indicative of the presence of a desired state of mind and a second physiological signal indicative of the absence of said desired state of mind, indicator means, and gate means for applying said first physiological signal to said indicator means to derive an indication in the absence of said second physiological signal and inhibiting said first physiological signal in the presence of said second physiological signal.

2. The biofeedback system of claim 1, wherein said indicator means comprises: an audio signal source, a modulator for modulating the signal of said audio signal in accordance with said first physiological signal in the absence of said second physiological signal to derive a modulated signal, and an acousto-electrical transducer responsive to the modulated signal.

3. The biofeedback system of claim 1 or 2, further comprising first and second auxiliary indicators respectively responsive to said first and second physiological signals for indicating the presence and absence of said signals.

4. A biofeedback system comprising, electrode means for deriving a single source signal from the scalp of a human subject, means for deriving a first physiological signal from a first frequency range of said source signal, means for deriving a second physiological signal from a second frequency range of said source signal, first detecting means for detecting when the amplitude of said first physiological signal is in a predetermined range, second detecting means for detecting when the amplitude of said second physiological signal exceeds a predetermined value, indicator means, and gate means for applying the output of said first detecting means to said indicator means to derive an indication in the absence of the output of said second detecting means and inhibiting the output of said first detecting means in the presence of the output of said second detecting means.

5. A biofeedback system as claimed in claim 4, wherein each of said means for deriving said first and second physiological signals comprises a bandpass filter connected to said electrode deriving means, a rectifier connected to the output of said bandpass filter and an integrator connected to the output of said rectifier to generate said first and second physiological signals.

6. A biofeedback system as claimed in claim 5, wherein the time constant value of said integrator associated with said first physiological signal deriving means is greater than the time constant value of the integrator associated with said second physiological signal deriving means.

7. A biofeedback system as claimed in claim 4, wherein said first frequency range is selected to detect a signal attributable to alpha brain waves.

8. A biofeedback system as claimed in claim 4, 5, 6 or 7, wherein the frequencies in said second range are higher than the frequencies in said first range.

9. A biofeedback system as claimed in claim 5, 6, 7 or 8, wherein said indicator means includes an audio program signal source, a modulator for modulating the signal of the program signal source in accordance with said first physiological signal in response to the absence of the output of said second detecting means to derive a modulated signal, and an acoustoelectrical transducer responsive to the modulated signal.

10. A biofeedback system as claimed in claim 4, 5, 6 or 7, further comprising first and second auxiliary indicators respectively responsive to outputs of said first and second detecting means for indicating the presence and absence of said outputs.

11. A biofeedback system as claimed in claim 10, wherein each of said auxiliary indicators comprises a visual indicator.

12. A method of indicating the state of mental activity of a human subject comprising placing electrodes on the head of the subject, said electrodes responding to brain activity of the subject to derive a signal including low frequency a.c. components having a maximum frequency of approximately 14 Hertz and high frequency a.c. components having a minimum frequency of approximately 80 Hertz, detecting the amplitudes of the high and low frequency components, and activating an indicator for the mental state activity only in response to the detected high frequency component having an amplitude less than a first predetermined level and the detected low frequency component having an amplitude greater than a first predetermined value and less than a second predetermined value.

13. A method as claimed in claim 12, wherein the indicator, when activated, indicates the detected level of the low frequency component.

14. A method as claimed in claim 13, wherein the indicator is an aural tone having a characteristic that is varied in response to the detected level of the low frequency component.

15. Apparatus for indicating the state of mental activity of a human subject comprising electrode means adapted to be placed on the head of the subject, said electrode means adapted to respond to brain activity of the subject to derive a signal including low frequency a.c. components having a maximum frequency of approximately 14 Hertz and high frequency a.c. components having a minimum frequency of approximately 80 Hertz, indicator means for detecting the amplitudes of the high and low frequency components, and means for activating the indicator means for the mental state activity only in response to the detected high frequency component having an amplitude less than a first predetermined level and the detected low frequency component having an amplitude greater than a first predetermined value and less than a second predetermined value.

16. An apparatus as claimed in claim 15, wherein the means for activating includes means for applying a signal indicative of the amplitude of the detected low frequency component to the indicator means.

17. An apparatus as claimed in claim 16, wherein the indicator means includes means for deriving an aural tone, and the means for activating includes means for varying a characteristic of the derived aural tone.

18. A method of indicating the state of mental activity of a human subject comprising placing electrodes on the head of the subject, said electrodes responding to brain activity of the subject to derive a signal including a low frequency a.c. components having a frequency range in the same low frequency range as alpha waves derived by the brain and high frequency a.c. components having a minimum frequency considerably higher than the highest frequency of the alpha waves, detecting the amplitudes of the high and low frequency components, and activating an indicator for the mental state activity only in response to the detected high frequency component having an amplitude less than a first predetermined level indicative of the subject not being in a state of relaxation and the detected low frequency component having an amplitude greater than a first predetermined value and less than a second predetermined value, the amplitude of the low frequency component between the first and second predetermined values being associated with the alpha waves.

19. A method as claimed in claim 18, wherein the indicator, when activated, indicates the detected level of the low frequency component.

20. Apparatus for indicating the state of mental activity of a human subject comprising electrode means adapted to be placed on the head of the subject, said electrode means adapted to respond to brain activity of the subject to derive a signal including low frequency a.c. components having a frequency range in the same low frequency range as alpha waves derived by the brain and high frequency a.c. components having a minimum frequency considerably high than the highest frequency of the alpha waves, indicator means for detecting the amplitudes of the high and low frequency components, and means for activating the indicator means for the mental state activity only in response to the detected high frequency component having an amplitude less than a first predetermined level indicative of the subject not being in a state of relaxation and the detected low frequency component having an amplitude greater than a first predetermined value and less than a second predetermined value, the amplitude of the low frequency component between the first and second predetermined values being associated with the alpha waves.

21. An apparatus as claimed in claim 20, wherein the means for activating includes means for applying a signal indicative of the amplitude of the detected low frequency component to the indicator.

22. An apparatus as claimed in claim 21, wherein the indicator means includes means for deriving an aural tone, and the means for activating includes means for varying a characteristic of the derived aural tone.

* * * * *